United States Patent
Edwards et al.

(10) Patent No.: US 7,463,714 B2
(45) Date of Patent: Dec. 9, 2008

(54) FOREIGN OBJECT DETECTION

(75) Inventors: Talion Edwards, Foristell, MO (US);
Gary Georgeson, Federal Way, WA
(US); Morteza Safai, Seattle, WA (US)

(73) Assignee: The Boeing Company, Chicago, IL (US)

( * ) Notice: Subject to any disclaimer, the term of this patent is extended or adjusted under 35 U.S.C. 154(b) by 177 days.

(21) Appl. No.: 11/550,292

(22) Filed: Oct. 17, 2006

(65) Prior Publication Data
US 2008/0095310 A1    Apr. 24, 2008

(51) Int. Cl.
*G01N 23/203* (2006.01)

(52) U.S. Cl. .......................... 378/87; 378/86

(58) Field of Classification Search .............. 378/57, 378/58, 86, 87, 88, 89, 90, 98.11, 98.12
See application file for complete search history.

(56) References Cited

U.S. PATENT DOCUMENTS

| | | | | | |
|---|---|---|---|---|---|
| 5,299,253 | A  * | 3/1994  | Wessels | ................. | 378/163 |
| 5,600,303 | A  * | 2/1997  | Husseiny et al. | ........ | 340/568.1 |
| 5,642,394 | A  * | 6/1997  | Rothschild | .............. | 378/57 |
| 5,763,886 | A  * | 6/1998  | Schulte | ............... | 250/358.1 |
| 6,094,472 | A  * | 7/2000  | Smith | .................... | 378/86 |
| 6,466,643 | B1 * | 10/2002 | Bueno et al. | .............. | 378/58 |
| 6,507,635 | B2 * | 1/2003  | Birdwell et al. | ............ | 378/58 |
| 6,614,872 | B2 * | 9/2003  | Bueno et al. | .............. | 378/58 |
| 6,618,465 | B2 * | 9/2003  | Mohr et al. | ............... | 378/58 |
| 6,636,581 | B2 * | 10/2003 | Sorenson | .............. | 378/58 |
| 6,665,373 | B1 * | 12/2003 | Kotowski et al. | ........... | 378/90 |
| 6,873,344 | B2 * | 3/2005  | Samra et al. | .............. | 715/723 |
| 6,895,073 | B2 * | 5/2005  | Shih et al. | ................. | 378/58 |
| 7,209,539 | B2 * | 4/2007  | De Smet | ................ | 378/57 |
| 7,266,174 | B2 * | 9/2007  | Birdwell et al. | ............ | 378/58 |

* cited by examiner

*Primary Examiner*—Allen C. Ho
(74) *Attorney, Agent, or Firm*—MacPherson Kwok Chen & Heid LLP

(57) ABSTRACT

A method and system for identifying foreign objection (FOD) in items such as aircraft are disclosed. The item may be imaged using x-ray backscatter before and after work is performed thereon. The image taken before work may be subtracted from the image taken after the work to provide a resultant image. The resultant image may indicate the presence of any FOD. Potential FOD in the resultant image may be checked against a database of known FOD to determine the identity thereof. By finding FOD, the occurrence of catastrophes such as aircraft crashes may be mitigated.

26 Claims, 3 Drawing Sheets

FOREIGN OBJECT DETECTION

TECHNICAL FIELD

The present invention relates generally to X-ray systems and, more particularly, to the use of X-ray backscatter to detect foreign objects in aircraft and other items.

BACKGROUND

Commercial and military aircraft are often modified in a manner that requires substantial disassembly and re-assembly of the aircraft. Such modification may involve the removal of exterior and/or interior panels to facilitate access to components of the aircraft that are contained within compartments located behind the panels.

When the panels are removed, foreign objects are often introduced into the compartments. Items such as tools, fasteners, manufacturing material, personal objects, and debris may be inadvertently left in such compartments after the modification is complete. Such items are commonly referred to as foreign object debris (FOD).

Thus, during modification of the aircraft there is the opportunity to unintentionally leave such items behind in the areas where work was done. This unfortunate opportunity also exists during original manufacture of the aircraft.

The presence of FOD in an aircraft is undesirable. FOD may interfere with the proper operation of critical aircraft systems. For example, FOD may foul cables or other mechanical devices that are used to control flight surfaces. FOD may also cause electrical shorts. It may also interfere with aircraft operation in a variety of other undesirable ways. Such interference may be costly and dangerous. It may inhibit proper operation of the aircraft to the point of causing a crash.

Once the panels are replaced, it is difficult to determine whether or not FOD is present. Although great care is generally taken to prevent the introduction of FOD into aircraft, the undesirable introduction of FOD into aircraft is unfortunately not an uncommon occurrence. The undesirable consequences of such introduction are also unfortunately not uncommon.

According to contemporary practice, technicians visually inspect work areas of aircraft prior to replacing panels. However, such visual inspection is too often insufficient. FOD may be and too often is overlooked.

As a result, there is a need for a method and system for determining if FOD is present on an aircraft. This is particularly true after modification of the aircraft, when the opportunity to inadvertently leave items such tools, manufacturing material, personal objects, and debris is present.

SUMMARY

Systems and methods are disclosed herein to provide for the detection of FOD. More particularly, according to an example of an embodiment of the present invention a method for detecting FOD may comprise scanning an item using x-ray backscatter prior to modifying the item so as to define a first image, scanning the item using x-ray backscatter subsequent to modifying the item so as to define a second image, and comparing the first and second images to determine the potential presence of FOD in the second image (and therefore in the item).

For example, FOD may be detected on a aircraft during manufacture or during maintenance procedures. As mentioned above, FOD is frequently introduced into aircraft during manufacture and maintenance procedures and may have catastrophic consequences if not detected and removed.

More specifically, in accordance with an example of an embodiment of the present invention, scanning the item may comprise scanning a portion of the item where the item was modified. For example, if maintenance work was only performed upon one wing of an aircraft, then only that wing may be scanned. Indeed, only the portion of the wing where a panel was removed may be scanned.

The first and second images may comprise two-dimensional images, three-dimensional images, or a combination of two-dimensional and three-dimensional images. Generally, the first and second images will comprise the same type of images, e.g., two-dimensional or three-dimensional. However, the first and second images may be different types of images. For example, a slice of data from a three-dimensional image may be compared to a two-dimensional image.

The first and the second images may be compared using pixel (or voxel) subtraction. That is, pixels of the first image may be subtracted from corresponding pixels of the second image. The subtraction may provide resultant pixel values. The resulting pixel values may be used to represent a brightness for a corresponding pixel in the resultant image.

The term pixel may be used herein to represent pixels and/or voxels. Thus, as used herein the term pixel may refer to a voxel, such as when the term is referring to a pixel of an image from a three-dimensional x-ray backscatter system Position relaxation may be used when comparing the first and second images. Position relaxation allows geometric features, as represented by groups of pixels, of one image to be moved so that they provide a better fit with respect to corresponding geometric features of another image. For example, position relaxation may be used on either the first image or the second image so as to facilitate mapping between the first and second images. In this manner, the first image may be more easily aligned or registered with respect to the second image.

A plurality of fiducials may be attached to the item prior to scanning the item to define the first and the second images. As those skilled in the art will appreciate, fiducials may facilitate registering the first image with respect to the second image. In this manner, processing of the first and second images may be more readily facilitated.

The first and/or second images may be processed prior to comparing the first and second images. Processing may make the first and second images more like one another while preserving information regarding the presence of any FOD. For example, such processing may comprise scaling and/or light balancing of the first and/or second images.

Portions of the resultant image may be compared to or otherwise checked against images or other information regarding FOD. In this manner, the presence of FOD may be determined and the identity of the FOD found may potentially be determined.

More particularly, the images or characteristics of suspected FOD may be compared to information within a database of known FOD. For example, when using an embodiment of the present invention to determine the presence of FOD in an aircraft after a maintenance procedure, the database of known FOD may comprise the tools and parts associated with the particular maintenance procedure that was performed.

The images or characteristics of any tools and/or parts that are unaccounted for at the completion of the maintenance procedure may be used for such a comparison. Such images or characteristics may be used either in place of or in addition to another database. In this manner, the identity of the FOD may potentially be more readily determined.

Geometric characteristics of known FOD may be compared to geometric characteristics of suspected FOD. More particularly, geometric characteristics of tools and material used in the modification procedure may be compared to geometric characteristics of potential FOD of the resultant image. For example, geometric characteristics of unaccounted for FOD may be compared to geometric characteristics of potential FOD in the resultant image.

According to an example of an embodiment, the present invention may comprise a system for determining the presence of FOD in an item. The system may comprise an x-ray backscatter scanner and an image comparator configured to compare two images from the x-ray backscatter scanner and to provide a resultant image.

The x-ray backscatter scanner may be configured to scan either an entire aircraft or portions of an aircraft. The x-ray backscatter scanner may be configured to provide two-dimensional images, three-dimensional images, or any desired combination of two-dimensional images and three-dimensional images.

The comparator may be configured to compare images via the use of pixel subtraction. The comparator may be configured to compare using position relaxation. Position relaxation allows comparisons to be made between substantially identical structures without minor changes in the structures giving false indications of the presence of FOD. Thus, small movements of structures, such as those due to thermal expansion/contraction, stress, and normal repositioning of movable mechanical components (such cables, linkages, etc.) are less likely to cause false positive indications of FOD.

The system may further comprise a plurality of fiducials configured to be attached to the item to facilitate registration of images from the x-ray backscatter scanner. Such fiducials may comprise x-ray absorbers or reflectors according to well known principles.

The system may further comprise a processor configured to process images from the x-ray backscatter scanner. The processor may process the images to make them more usable by the comparator. The processor may process the images to make them more like one another in a manner that does not inhibit determination of the presence of FOD. The images may be made more like one another in a manner that makes the non-FOD portions thereof tend to cancel during the comparison. For example, the processor may provide scaling and/or white balance.

The system may further comprise a database of FOD images and/or of FOD geometric characteristics. The system may also further comprise a geometry comparator configured to compare FOD characteristics to potential FOD in the resultant image.

One or more embodiments of the present invention provide a method and system for determining if FOD is present on an aircraft. Thus, potentially dangerous and life threatening situations may be avoided by locating and removing such FOD.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Examples of embodiments of the present invention and their advantages are best understood by referring to the detailed description that follows. It should be appreciated that like reference numerals are used to identify like elements illustrated in one or more of the figures.

DETAILED DESCRIPTION

Figure 1:
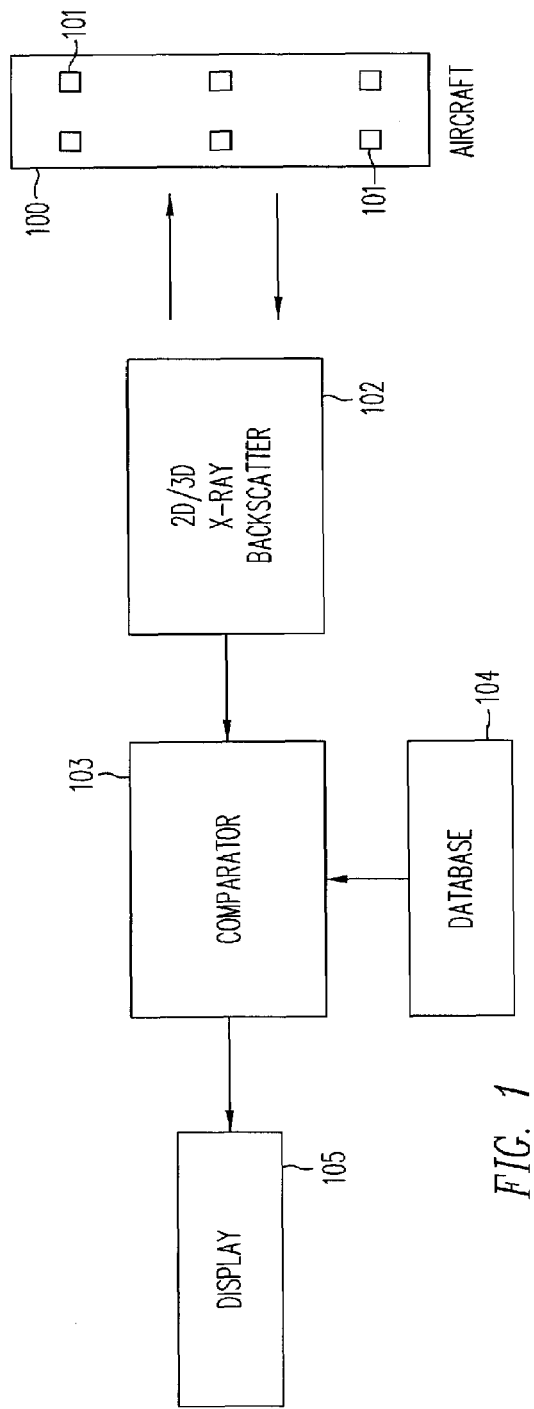
FIG. 1 shows a block diagram illustrating a foreign object detection system in accordance with an example of an embodiment of the present invention.

The presence of foreign objects (FOD) in an aircraft may present a substantial hazard to the aircraft, as well as to its cargo, crew, and passengers. Therefore, it is desirable to determine if any FOD is present Further, the ability to readily locate FOD in an aircraft may eliminate the need for an exhaustive search of the aircraft, such as may be necessitated when a tool or other item is determined to be missing and to likely be somewhere in the aircraft. According to contemporary practice, such a search may involve partial disassembly of the aircraft and may thus cause an undesirable delay in delivery of the aircraft, as well as undesirably increased labor costs that are associated with searching the aircraft.

The output from an X-ray backscatter system may be a projected 2D grayscale image. Differences between an image of an aircraft taken before a modification and an image taken after the modification are generally those caused by the addition of newly installed hardware, and those caused by the elimination of removed hardware. Any other differences in the images may potentially be FOD.

An example of an embodiment of the present invention comprises a process for using pixel subtraction to automatically discern differences between pre-modified aircraft and post-modified aircraft. A resultant image from a pixel subtraction between the two aircraft states may include newly installed hardware, deleted hardware, and FOD. A modification or manufacturing engineer familiar with the subject modification may discern between design hardware and FOD. Alternatively, an automated process may be used to discern between design hardware and FOD, as discussed below.

An exemplary embodiment of this process may comprise taking an x-ray backscatter image of areas of interest prior to aircraft modification. These images may be stored until the modification is complete. In order to supplement the detection process, current best practices of tool inventory and FOD accounting may be retained. After the modification is complete, a second x-ray backscatter image may be taken.

Photo editing software may be used to register the before and after images with respect to one another and to perform any image processing that is required (such as scaling, light balancing, etc.) This process may be either manual (performed by a human operator) or automatic (performed by a computer or the like). Position relaxation on the initial image will allow features to be shifted so that they may be mapped on top of themselves to reduce discrepancies due to minor differences in the two scans. Fiducials may be rigidly located in the aircraft to facilitate image registration. When possible, the fiducials remain in place throughout the modification process, so that their precise positioning is not disturbed.

Once the images are registered, pixel subtraction may be performed wherein each pixel in the before image is subtracted from the corresponding pixel in the after image. The resulting pixel value may be used to represent the brightness for that pixel in a resultant Image. The resultant image may then be analyzed to determine the presence of potential or suspected FOD, such as by using FOD inventory list or database as a reference.

One or more embodiments of the present invention may be used to detect FOD in critical areas such as flight control areas, fuel systems, and life support systems in a new production environment. A scan of a reference assembly, known to be free of FOD, may be used as the before state. An inline production process may then be used to automatically detect any deviation from the reference state.

A significant additional benefit of at least one embodiment of the present invention is the enhanced ability to provide post-modification configuration documentation. Because the resultant image should contain only parts that were changed on the aircraft, the data represent the explicit product of the culmination of all design, planning, and manufacturing definition that defined the modification. This information may be stored to be used for future modification designs, or service bulletin development.

One or more embodiments of the present invention may be used to verify and document modifications that have been performed. This may be accomplished by providing x-ray backscatter images of critical modifications. Before and after images may be provided.

Examples of embodiments of the present invention are shown in FIGS. 1-4 and are discussed in detail below.

FIG. 1 shows a flow chart of a foreign objection detection system according to an example of an embodiment of the present invention. An object, such as an aircraft 100, may be fitted with one or more fiducials 101. Typically, a plurality of fiducials 101 will be attached to aircraft 100. Fiducials 101 may be either temporarily or permanently attached to aircraft 100. They may be either inside, outside, or any combination of inside and outside of the aircraft 100. Fiducials 101 are attached to aircraft 100 prior to modifying aircraft 100. Fiducials 101 are located in a manner that facilitates enhanced alignment of x-ray backscatter images of the aircraft 100 or at least one portion thereof.

Fiducials 101 are attached to aircraft 100 in a manner that assures that fiducials 101 remain in place throughout modification of aircraft 100. For example, fiducials 101 may be attached to aircraft 100 via adhesive bonding, such as via superglue, dental cement, or epoxy. As a further example, fiducials 101 may be attached to aircraft 100 via fasteners, such as bolts or screws.

Fiducials 101 facilitate alignment of images that are used to detect the presence of FOD, as discussed in detail below. The use of fiducials 101 is optional. Other means for aligning the images may alternatively be used.

A two-dimensional and/or a three-dimensional x-ray backscatter system 102 may be used to provide images that are used to determine the potential presence of FOD in aircraft 100 after modification thereof. Such use of two-dimensional/three-dimensional x-ray backscatter system 102 is discussed in detail below.

An image taken after modification of aircraft 100 is compared to an image taken prior to modification of aircraft 100 by comparator 103. Such comparison may be performed by pixel subtraction, for example. Thus, each pixel of the image taken prior to modification of aircraft 100 may be subtracted from a corresponding pixel of the image taken after modification of aircraft 100 to provide a resultant image. Pixel subtraction may result in a resultant image that contains differences between the two images. Such differences may be due to the presence of FOD in aircraft 100.

Optionally, a database 104 containing geometric characteristics of known (previously identified and characterized) FOD may be used to attempt to identify any potential FOD in the resultant image. Thus, geometric characteristics of potential FOD in the resultant image may be compared to geometric characteristics of known FOD in database 104 to attempt to determine if the potential FOD is actually FOD. Such geometric characteristics may include size (such as largest dimension), shape, volume, key dimensions, ratios of dimensions, and/or the presence of unique structures (such as backscatter targets that may be present in some items such as tools to make them more apparent on backscatter images).

The results of the comparison of the image taken prior to modification and the image taken after modification may be shown on a display 105. Such results may include the resultant image, information representative of that provided by the resultant image (which may be in a graphic or text format), and/or information resulting from use of database 104. For example, the results may indicate that a specific tool that was used during modification of aircraft 100 is still on aircraft 100, hidden in a closed compartment thereof, after modification is complete. As discussed above, the presence of such FOD may present a substantial hazard.

Figure 2:
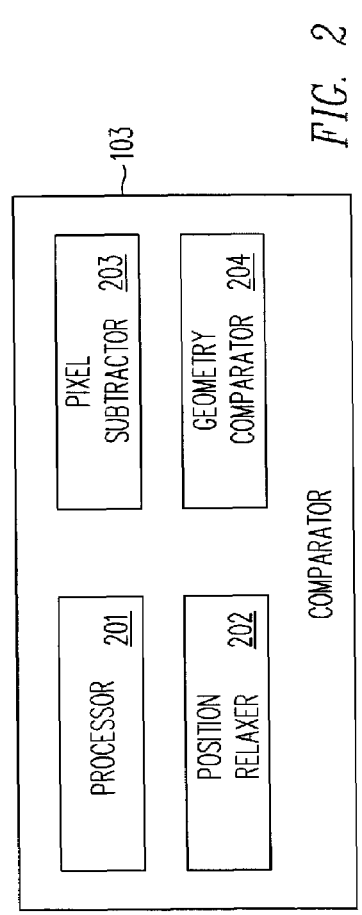
FIG. 2 shows a block diagram illustrating the comparator of FIG. 1 in further detail.

FIG. 2 shows comparator 103 in further detail. Comparator 103 may comprise a processor 201, a position relaxer 202, a pixel subtractor 203, and/or a geometry comparator 204. Processor 201, position relaxer 202, pixel subtractor 203, and/or geometry comparator 204 may be implemented either in hardware (such as via dedicated circuitry) or in software (such as via a general purpose microprocessor), or in any combination of hardware and software.

Processor 201 may perform processing tasks such as scaling and light balance. Position relaxer 202 may vary, to some degree, the size, shape, and/or position of geometric structures of the image taken before modification and/or the image taken after modification, so as to better facilitate a match of such structures by comparator 103. In this manner, minor differences between the two images are less likely to result in contributions to the resultant image. Such minor differences may result from thermal expansion, mechanical stress, and/or movement of non-rigid components (cables, wiring, plumbing, etc.). Thus, the use of position relaxer 202 makes it more likely that items that appear in the resultant image will be FOD (it reduces the occurrence of false positives).

As discussed above, pixel substractor 203 performs pixel subtraction to provide the resultant image. Generally, each pixel of one of the images is subtracted from a corresponding pixel of the other image. However, the use of position relaxer 202 may result in pixels being subtracted from other, generally nearby, pixels instead. In any event, position relaxer 202 attempts to cause a structure in one image to be subtracted from the same structure in another image even though the structure is not represented by the same pixels in each image.

Geometry comparator 204 compares the geometric characteristics of items found in the resultant image to geometric characteristics of known FOD using database 104. Items that are suspected to be missing and that are therefore good candidates for FOD may be given priority during this comparison. For example, if a particular tool cannot be located after modification of aircraft 100, then geometry comparator may give preference to that tool as being an item shown in a resultant image if geometric characteristics of the item in the image are generally consistent with those of the missing tool.

Figure 3:
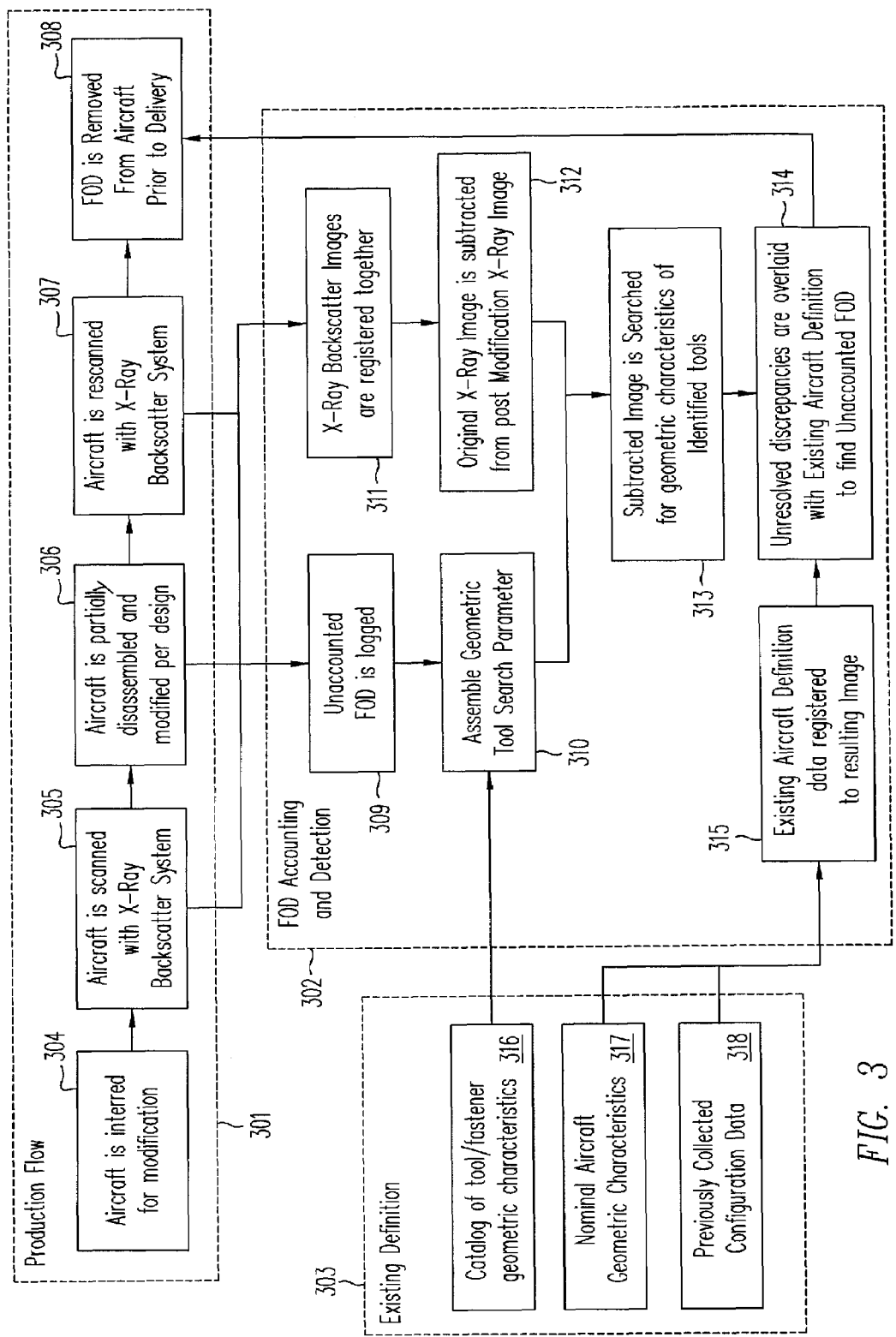
FIG. 3 shows a flow chart illustrating an example of an embodiment of the present invention.

FIG. 3 shows a flow chart of an example of an embodiment of the foreign objection detection system of the present invention. Production flow 301 is the flow of the product through its production process, e.g., modification thereof. The product is the item within which the presence of foreign objects is a concern. In the illustrated example, the item is an aircraft and the production process is a modification thereof (such as may occur during manufacture, maintenance, or upgrading of the aircraft).

Production flow 301 comprises interring the aircraft 100 for modification, as indicated in block 304. The aircraft 100 may be interred at the manufacture's facility or at some other maintenance depot. Indeed the aircraft 100 may be interred anywhere that modification may be performed.

Prior to modification of the aircraft 100, the aircraft 100 is scanned, such as using a two-dimensional and/or three dimensional x-ray backscatter system 102 (FIG. 1), as shown in block 305. Then, the aircraft is partially disassembled and modified per the desired design, as indicated in block 306. After modification the aircraft 100 is again scanned, such as in the same manner as before, as indicated in block 307. Any FOD identified by the practice of the present invention may be removed, as indicated in block 308.

FOD accounting and detection 302 provides a way to determine the likely presences of FOD within aircraft 100 and a way to potentially identify the FOD. The image formed by scanning the aircraft 100 with the x-ray backscatter system per block 305 is registered with respect to the image formed by scanning the aircraft 100 with the x-ray backscatter system per block 307, as indicted in block 311. Such registration is necessary so that the two images may be properly compared to one another, such as via pixel subtraction. Position relaxation may be used, as discussed herein.

The original x-ray image (taken per block 305) may be subtracted from the post modification x-ray image 312 (taken per block 307) to form a resultant or subtracted image, as indicated in block 312. The subtracted image may then be searched for geometric characteristics of identified tools, as indicated in block 313. Such searching may be facilitated by logging of unaccounted FOD, as indicated in block 309, and by assembling geometric tool search parameters, as indicated in block 310. The assembled geometric tool search parameters are defined by geometric characteristics of known FOD and may be the search parameters used to identify the potential presence of FOD in the resultant image.

The location of potential FOD that was identified by comparison of the two images may be facilitated by overlaying unresolved discrepancies between the two images with an existing aircraft definition, such as a computer aided drawing (CAD) drawing of the aircraft, as indicated in block 314. In this manner, a user of the system may be provided with a drawing that identifies the location of any potential FOD within the aircraft 100. That is, a drawing of the aircraft 100 may be provided that has indicia formed thereto to indicate the location and type of FOD. The type of FOD may be indicated via the use of unique icons for each type of FOD (a tool icon for tool FOD, a fastener icon for fastener FOD, etc.).

Existing definitions of geometric characteristic may be used to facilitate FOD location and identification, as indicated in block 303. A catalog of tool, fastener, and other potential FOD geometric characteristics may be compiled, as indicated in block 316. This information may be used to define the geometric tool search parameters per block 310.

Further, nominal aircraft geometric characteristics may be provided, as indicated in block 317, and previously collected configuration data may be provided, as indicated in block 318. The aircraft geometric characteristics of block 317 and the configuration data of block 318 may be used to provide the existing aircraft definition data of block 315.

Thus, geometric data of the aircraft and geometric data of potential FOD may be used to facilitate the finding and identification of FOD in the resulting image and to facilitate the determination of the location of such FOD within the aircraft 100.

Figure 4:
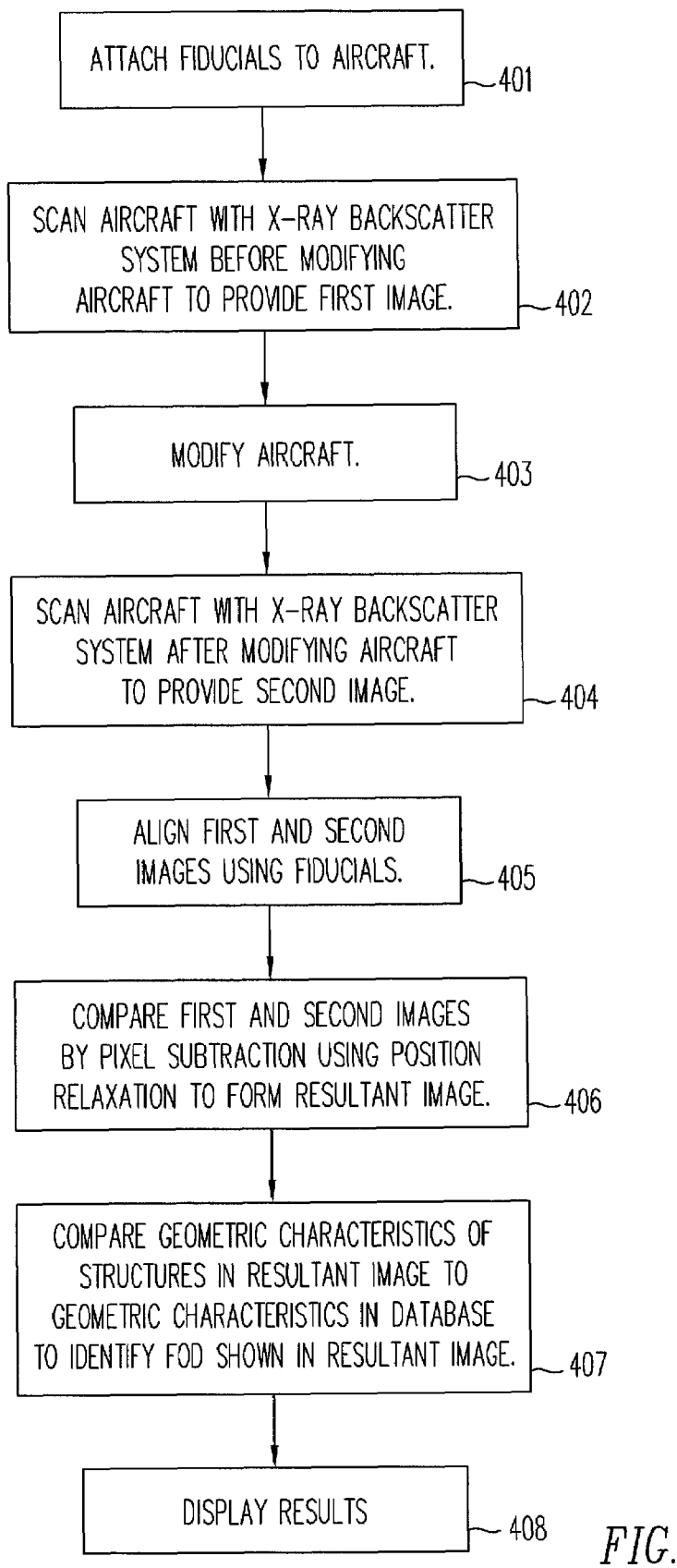
FIG. 4 shows a flow chart illustrating another example of an embodiment of the present invention.

FIG. 4 shows an example of an embodiment of the present invention. Fiducials may be attached to the aircraft 100, as discussed above and as indicated in block 401. The aircraft may then be scanned, such as with one-dimensional and/or two-dimensional x-ray backscatter, as indicated in block 402. After this initial scanning, the aircraft may be modified as indicated in block 403. Then, the aircraft is again scanned, generally using the same equipment and procedure used for the initial scan, as indicated in block 404.

The two images resulting from the two scans may be aligned using the fiducials as indicated in block 405 and compared as indicated in block 406. Of course, many initial images and many final images may be necessary, depending upon the size of the area modified and the size of the area subject to each scan.

As discussed above, position relaxation may be used to better facilitate such comparison. As indicated in block 407, the geometric characteristics of any structures found in the resultant image(s) may be compared to geometric characteristic in a database to determine if items in the resultant image are FOD (as opposed to desired aircraft structures). As indicated in block 408, the results of the comparison are displayed or otherwise communicated so that a user may check the aircraft to verify the presence of FOD found according to this process and may then remove the FOD, as indicated in block 308 of FIG. 3.

Embodiments of the present invention are described herein as using x-ray backscatter to facilitate scanning for FOD. However, those skilled in the art will appreciate that other technologies may be used to facilitate scanning for FOD. For example, gamma ray backscatter may similarly be used and can thus be consider equivalent to x-ray backscatter. Thus, the discussion of x-ray backscatter is by way of example only, and not by way of limitation.

Embodiments of the present invention are described herein as having application to the detection of FOD on aircraft. However, those skilled in the art will appreciate that embodiments of the present invention may similarly have application to the detection of FOD in a variety of other vehicles, objects, or areas. For example, embodiments of the present invention may be used to detect FOD in automobiles, ships, submarines, satellites and spacecraft. As a further example, embodiments of the present invention may be used to detect FOD in food products, such as boxed or canned foods. As such, discussion of embodiments of the present invention as having application to the detection of FOD in aircraft is by way of example only, and not by way of limitation.

Thus, methods and systems are provided for locating FOD on an aircraft or the like. After being located, the FOD may be removed such that it does not present a hazard to the aircraft, cargo, crew, or passengers.

Embodiments described above illustrate but do not limit the invention. It should also be understood that numerous modifications and variations are possible in accordance with the principles of the present invention. Accordingly, the scope of the invention is defined only by the following claims.

We claim:

1. A method for detecting foreign object debris (FOD) in an item that has been modified, the method comprising:
   scanning the item using x-rays prior to modifying the item;
   detecting x-rays backscattered from the unmodified item;
   forming a first image of the unmodified item from the backscattered x-rays detected;
   modifying the item;

scanning the item using x-rays subsequent to modifying the item detecting x-rays backscattered from the modified item;

forming a second image of the modified item from the backscattered x-rays detected;

comparing the first image and the second image so as to define a resultant image depicting potential FOD in the modified item;

determining geometrical characteristics of the potential FOD from the resultant image; and, comparing the geometrical characteristics of the potential FOD with previously stored values of at least one of the group consisting of known FOD geometric characteristics, nominal item geometric characteristics and previously collected item geometric configuration data to ascertain whether the potential FOD comprises actual FOD.

2. The method as recited in claim 1, wherein the item comprises an aircraft.

3. The method as recited in claim 1, wherein scanning the item comprises scanning a portion of the item where the item was modified.

4. The method as recited in claim 1, wherein modifying the item is a procedure for manufacturing the item.

5. The method as recited in claim 1, wherein modifying the item is a procedure for maintaining the item.

6. The method as recited in claim 1, wherein defining the first image and the second image comprises defining two-dimensional images.

7. The method as recited in claim 1, wherein comparing the first image and the second image comprises comparing the first image and the second image using pixel subtraction.

8. The method as recited in claim 1, wherein comparing the first image and the second image comprises subtracting pixels in the first image from corresponding pixels in the second image.

9. The method as recited in claim 1, wherein comparing the first image and the second image comprises subtracting pixels in the first image from corresponding pixels in the second image and using the resulting pixel values to represent a brightness for corresponding pixels in a resultant image.

10. The method as recited in claim 1, wherein comparing the first image and the second image comprises using position relaxation on at least one of the first image and the second image so as to facilitate mapping between the first image and the second image.

11. The method as recited in claim 1, further comprising registering the first image with respect to the second image to facilitate comparing the first image and the second image.

12. The method as recited in claim 1, further comprising attaching a plurality of fiducials to the item prior to scanning the item to define the first image and the second image, so as to facilitate registering the first image with respect to the second image.

13. The method as recited in claim 1, further comprising processing at least one of the first image and the second image prior to comparing the first image and the second image, the processing making the first image and the second image more like one another while preserving information regarding the presence of any FOD.

14. The method as recited in claim 1, further comprising processing at least one of the first image and the second image prior to comparing the first image and the second image, the processing comprising scaling.

15. The method as recited in claim 1, further comprising processing at least one of the first image and the second image prior to comparing the first image and the second image, the processing comprising light balancing.

16. A system for determining the presence of foreign object debris (FOD) in an item, the system comprising:

an x-ray backscatter scanner;

an image comparator configured to compare two images from the x-ray backscatter scanner and to provide a resultant image; and, a database of known FOD geometric characteristics.

17. The system as recited in claim 16, wherein the x-ray backscatter scanner is configured to scan at least portions of an aircraft.

18. The system as recited in claim 16, wherein the x-ray backscatter scanner is configured to provide two-dimensional images.

19. The system as recited in claim 16, wherein the comparator is configured to compare via pixel subtraction.

20. The system as recited in claim 16, wherein the comparator is configured to compare using position relaxation.

21. The system as recited in claim 16, further comprising a plurality of fiducials configured to be attached to the item to facilitate registration of images from the x-ray backscatter scanner.

22. The system as recited in claim 16, further comprising a processor configured to process images from the x-ray backscatter scanner.

23. The system as recited in claim 16, further comprising a processor configured to process images from the x-ray backscatter scanner by scaling and/or light balancing the images.

24. The system as recited in claim 16, further comprising a geometry comparator configured to compare actual FOD geometric characteristics to potential FOD geometric characteristic that are present in the resultant image.

25. A system for determining the presence of foreign object debris (FOD) in an item, the system comprising:

means for scanning the item with x-rays and for forming images from the x-rays backscattered therefrom during the scanning;

means for scaling and light balancing the images;

means for comparing two of the images so as to define a resultant image depicting potential FOD in the modified item;

means for generating geometric characteristics of the potential FOD depicted;

means for storing known FOD geometric characteristics; and, means for comparing the stored known FOD geometric characteristics to the potential FOD geometric characteristics.

26. A system for determining the presence of foreign object debris (FOD) in an item, the system comprising:

an x-ray backscatter scanner;

an image comparator configured to compare two images from the x-ray backscatter scanner and to provide a resultant image; and, a geometry comparator configured to compare actual FOD geometric characteristics to the geometric characteristics of potential FOD present in the resultant image.

* * * * *